United States Patent [19]

Feldmann et al.

[11] Patent Number: 4,564,692

[45] Date of Patent: Jan. 14, 1986

[54] PROCESS FOR RECOVERING PURE CRYSTALLINE MONOANHYDROHEXITOLS AND DIANHYDROHEXITOLS

[75] Inventors: John Feldmann, Krefeld, Fed. Rep. of Germany; Hubert Koebernick, Wyckoff, N.J.; Klaus Richter, Meerbusch-Boesinghoven; Hans-Ulrich Woelk, Hamburg, both of Fed. Rep. of Germany

[73] Assignee: CPC International Inc., Englewood Cliffs, N.J.

[21] Appl. No.: 514,731

[22] Filed: Jul. 18, 1983

[30] Foreign Application Priority Data

Aug. 14, 1982 [DE]  Fed. Rep. of Germany ....... 3230349

[51] Int. Cl.$^4$ .................. C07D 493/04; C07D 307/20
[52] U.S. Cl. ...................... 549/464; 549/476
[58] Field of Search ................................ 549/464, 476

[56] References Cited

U.S. PATENT DOCUMENTS

| | | | |
|---|---|---|---|
| 2,315,699 | 4/1943 | Goepp, Jr. | 568/868 |
| 2,390,395 | 12/1945 | Soltzberg | 549/476 |
| 3,160,641 | 12/1964 | Hartmann | 549/464 |
| 3,484,459 | 12/1969 | Hartmann | 549/477 |
| 4,313,884 | 2/1982 | Arena | 549/464 |

OTHER PUBLICATIONS

Hockett et al., J.A.C.S., vol. 68, pp. 927–930, (1946).
Tipson, Technique of Org. Chem., vol. III, Part I, Separation and Purification—Editor Weissberger, (1956), Chapter III, pp. 395–398, 485–490 and 512–514.
Beilstein's Handbuch der Organischen Chemie, 4th Ed., 1933, vol. 17, p. 191.
Hockett et al., *J. Am. Chem. Soc., 68, 927–935, (1946)*.

*Primary Examiner*—Henry R. Jiles
*Assistant Examiner*—Bernard I. Dentz

[57] ABSTRACT

A simplified economical process is provided for preparing pure anhydro sugar alcohols by a controlled crystallization from concentrated aqueous solutions or melts containing these alcohols. These pure anhydro sugar alcohols are useful as polyol components in making polyester and polyurethane polymers.

19 Claims, No Drawings

PROCESS FOR RECOVERING PURE CRYSTALLINE MONOANHYDROHEXITOLS AND DIANHYDROHEXITOLS

FIELD OF THE INVENTION

The invention relates to a process for the isolation of pure anhydro sugar alcohols by crystallization from a concentrated solution.

BACKGROUND OF THE INVENTION

It has been known for some time that when sugar alcohols are dehydrated by means of acid catalysts they form one or more anhydro sugar alcohols. In particular, when the hexitols, sorbitol and mannitol, are dehydrated, they give mixtures of mono and dianhydrohexitols. Such compounds are useful as polyol components in making polyester and polyurethane polymers. However, previous processes for the purification of such compounds have been so costly that they have found comparatively little use in the making of polymers.

When sugar alcohols are dehydrated, the reaction mixtures frequently contain, in addition to the desired products, various degradation products and the products of secondary reactions, as well as unconverted starting materials, solvents and catalysts or their neutralization products. Although some impurities may be present in only small amounts, such impurities are detrimental to their use in specific reactions, particularly in the production of polyesters.

The first step in purification of anhydro sugar alcohols is usually accomplished by methods used in sugar chemistry which involve treatment of their solutions with such materials as activated carbon and ion-exchange resins. The anhydro sugar alcohols are then isolated from the partially purified reaction mixture by multi-step processes. These commonly include a preliminary separation by means of chromatography, and extraction or fractional distillation under reduced pressure. Further purification is achieved by fractional crystallization of the material from solvents such as ethyl acetate or lower aliphatic alcohols.

One process which has been disclosed for the purification of anhydro sugar alcohols involves the removal of impurities by complexing them with the borate ion before distillation (U.S. Pat. No. 3,160,641). Another process employs converting the crude dehydration mixture into acetal derivatives by means of an aldehyde or ketone. The acetal derivatives are then separated and the purified materials are regenerated from their acetals (U.S. Pat. No. 3,484,459).

Even these complicated and expensive purification procedures frequently fail to give a product of sufficient purity for a specific use, or the yields of purified product are so low that the process is not economical. In particular, residual amounts of crystallization solvents, such as ethyl acetate, make them unsuitable for certain uses, such as the manufacture of polyesters.

SUMMARY OF THE INVENTION

It is an object of the invention, therefore, to provide a simplified economical process for producing pure crystalline anhydro sugar alcohols which overcomes the disadvantages of the prior processes. It is a further object of this invention to provide a process whereby pure crystalline anhydro sugar alcohols can be obtained without the use of organic crystallization solvents. Still another object of this invention is to provide a process for obtaining pure anhydro sugar alcohols from reaction mixtures that have only been prepurified by means of ion exchangers and/or activated carbon.

In accordance with this invention, there is provided a process for recovering a pure crystalline anhydro sugar alcohol selected from the group consisting of anhydropentitols, monoanhydrohexitols and dianhydrohexitols. The crystalline alcohol is recovered from an aqueous mixture of which at least 40% by weight on a dry solids basis is the desired anhydro sugar alcohol. This is accomplished by means of the following sequential steps:

(a) concentrating the mixture to a heavy liquor with a dry solids content of at least 70% by weight;
(b) adjusting the temperature of the concentrated mixture to not more than 70° C.;
(c) inoculating the concentrated mixture with at least 0.1% by weight of the mixture of seed crystals of the desired anhydro sugar alcohol;
(d) stirring the inoculated mixture at such a rate as to promote crystallization of the anhydro sugar alcohol;
(e) maintaining the supersaturation of the mixture with respect to the anhydro sugar alcohol being crystallized in the range where the existing crystals continue to grow without the spontaneous formation of new seed crystals; and
(f) separating the crystalline anhydro sugar alcohol from the mixture.

DETAILED DESCRIPTION OF THE INVENTION

The process of this invention is directed to the purification of the anhydro sugar alcohols: anhydropentitols, monoanhydrohexitols and dianhydrohexitols. This invention is made possible by the discovery that these anhydro sugar alcohols, in spite of their extremely high water solubility compared to the corresponding sugar alcohols and sugars, can be crystallized from aqueous solutions or melts at a comparatively high degree of selectivity and purity. Crystallization is possible even from solutions with a dry solids content of no more than about 70% by weight. Such solutions are referred to herein as heavy liquors.

In carrying out the process of this invention, it is preferable to use heavy liquors with a water content of from 1% to 20% by weight. It is more preferable to use a heavy liquor with a water content of from 2% to 15% by weight, and it is most preferable to use a heavy liquor having a water content of from 3% to 8% by weight.

Surprisingly, the anhydro sugar alcohol can be crystallized from heavy liquors in which its concentration is comparatively low. For example, it can be crystallized from an aqueous mixture in which as little as 40% by weight on a dry solids basis is the desired anhydro sugar alcohol. However, it is preferred to use a mixture which contains from about 50% to about 99% by weight of the anhydro sugar alcohol on a dry solids basis. A more preferred mixture is one that contains from about 60% to about 95% by weight of the anhydro sugar alcohol on a dry solids basis, and it is most preferred to use a mixture which contains from about 75% to about 90% by weight of the anhydro sugar alcohol on a dry solids basis.

The process of this invention is accomplished by adding seed crystals of the desired anhydro sugar alcohol to the heavy liquor. The amount of seed crystals used in the process of this invention can be surprisingly low. The required level of seed crystals in some cases, under otherwise favorable conditions, can be as low as about 0.1% by weight although larger amounts are, of course, more expedient from a technical point of view. Experience has shown that it is recommended for the purpose of this invention to inoculate the heavy liquor with from 0.2% to 20% by weight, preferably from 0.5% to 10% by weight, and more preferably from about 1% to about 5%, by weight of the mixture, of crystals of the desired anhydro sugar alcohol.

Because of the high solubility of the anhydro sugar alcohols in water, the temperature at which the crystallization is carried out is relatively low. The temperature of the mixture, even in the initial phase, should not be more than about 70° C. On the other hand, extremely low temperatures will cause difficulties even in the final phase of the crystallization. And so, as a matter of experience, it has been found advisable to carry out crystallization at temperatures between about 20° C. and 65° C., preferably at temperatures between 25° C. and 60° C., and more preferably at temperatures between 30° C. and 55° C.

In carrying out the process of this invention, the heavy liquor, which has been inoculated with crystals of the desired anhydro sugar alcohol, is allowed to crystallize with stirring. The process can be carried out either under isothermal conditions or with temperatures declining during the course of crystallization. Whichever method is used the supersaturation of the mixture with respect to the anhydro sugar alcohol being crystallized is maintained in the range where the existing crystals can continue to grow without the spontaneous formation of new seed crystals.

Crystallization under isothermal conditions is simpler in most cases because constantly changing temperatures are difficult to control on an industrial scale. On the other hand, crystallization with slowly declining temperatures, at least when applied in a one-step process, usually leads to higher crystal yields. It is frequently useful to use a combination of the two processes whereby crystallization is carried out under isothermal conditions during the initial phase of the crystallization and then the temperature is graudally decreased during the final phase of crystallization to obtain higher yields.

When the temperature is reduced during the course of crystallization, the temperature of the mixture is lowered at a rate not to exceed 0.1° C. per minute. Preferably, the temperature of the mixture is lowered at a rate between about 0.01° C. per minute and 0.05° C. per minute.

When the process of the invention is carried out under isothermal conditions, the supersaturation of the mixture can be maintained in the desired range by evaporating water from the mixture. Alternatively, the supersaturation of the mixture can be maintained by adding additional heavy liquor to the mixture. For the purpose of this invention, it is preferable as a rule to keep the degree of supersaturation low and more or less constant, particularly when trying to obtain relatively high yields of crystallization in one cycle, when using heavy liquors of comparatively low purity, or when employing small amounts of seed crystals.

We have found, surprisingly, that it is not necessary to keep the degree of supersaturation low and more or less constant, especially during the initial phase of crystallization. Thus, the heavy liquor, prior to inoculation, can be rendered highly supersaturated by concentrating and/or cooling. The supersaturation then gradually disappears during the course of crystallization. While this mode of operation will not give optimum yields per cycle, it is preferred in certain cases because, as shown by experience, it permits comparatively high rates of crystallization. This is illustrated in Example 3.

Suitable heavy liquors are, basically, all aqueous anhydro sugar alcohol solutions having a suitable concentration regardless of how they are obtained. For the purposes of this invention, however, we prefer to use a reaction product obtained by acid-catalyzed dehydration of pentitols, hexitols, or monoanhydrohexitols. The acid-catalyzed dehydration is conveniently carried out by heterogeneous acid catalysts according to one of the processes described in German OSes Nos. P 30 41 626 and P 30 41 673. Such reaction mixtures can be used either directly or after purification, decolorization and/or adjustment to a water content of a most 30% by weight according to methods commonly used in sugar technology.

The process of the invention can be carried out batchwise or continuously and in one or several steps. In the multi-step embodiments, the different steps can be performed separately in an individual crystallizer or successively in one or several crystallizers.

The crystalline anhydro sugar alcohols are separated from the mixture by any conventional means such as centrifugation or filtration. The separated crystalline anhydro sugar alcohol can be washed with a small amount of water or with an aqueous solution of the anhydro sugar alcohol.

The mother liquor from which the crystalline anhydro sugar alcohol is separated can be further concentrated and treated as in the original process to give an additional crop of the crystalline anhydro sugar alcohol. If the heavy liquors contain two or more different anhydro sugar alcohols, it is possible under certain conditions to obtain two or three different anhydro sugar alcohols in succession in pure crystalline form by fractional crystallization. This is done by first inoculating the heavy liquor with crystals of a first anhydro sugar alcohol and allowing it to crystallize until a second anhydro sugar alcohol has been enriched in the mother liquor to more than 40% by weight based on the dry matter. After the mother liquor is separated from the crystals of the first anhydro sugar alcohol, that liquor can be concentrated if necessary and inoculated with crystals of the enriched second anhydro sugar alcohol and the crystallization process repeated.

If the mother liquor contains sugar alcohols which have not been dehydrated, the mother liquor can be subjected to an acid-catalyzed dehydration to convert this material into anhydro sugar alcohols. The crystalline anhydro sugar alcohols are then isolated from the dehydration reaction mixture according to the general process of the invention.

The following examples further illustrate the process of this invention. The anhydro sugar alcohol mixtures used in these examples were reaction products obtained from the corresponding sugar alcohols by acid-catalyzed dehydration with strongly acidic cationic-exchange resins in the $H^+$ form. (These are generally macroporous polystyrene sulfonic acid resins cross-linked with about 14% of divinyl benzene.) The reaction product mixtures were prepurified and decolorized by treatment with ion exchangers as well as with activated carbon. The mixtures were concentrated by vacuum evaporation to the water content given in the example.

EXAMPLE 1

Into a crystallizer equipped with slowly rotating agitator and double jacket for heating and cooling was placed 3200 g of an anhydro sugar alcohol mixture. This contained 3% by weight of water and 82% by weight of the dry substance was dianhydro sorbitol. The heavy liquor was placed in the crystallizer at a temperature of 53° C. and cooled to 45° C. Then it was inoculated, under constant stirring, with 10 g of 1,4:3,6-dianhydro-D-sorbitol (granules about 0.3–0.9 mm diameter), and the mixture was gradually cooled to 35° C. during 16 hours with slow stirring. The crystals were separated from the mother liquor by centrifuging and purified by washing with a small amount of cold water (about 50 ml).

The yield of 1,4:3,6-dianhydro-D-sorbitol was 1270 g (49.9% of theory). It had the following properties:
Purity (HPLC): Greater than 99%
Melting Point: 62.5° C.
Rotation: $[a]_D^{20} = +45°$ C. (c=0.8; H$_2$O)
Water Content: Less than 0.5%

EXAMPLE 2

Example 1 was repeated except that 100 g of heavy liquor with a dianhydro sorbitol content of 84% by weight, based on dry matter, was placed in the crystallizer and 5 g of seed crystals were added. The mixture was cooled from 45° C. to 35° C. during 8 hours.

The yield of 1,4:3,6-dianhydro-D-sorbitol was 41.2 g (49.1% of theory). It had the following properties:
Purity (HPLC): Greater than 99%
Melting Point: 60.8° C.
Rotation: $[a]_D^{20} = +44.3°$ C. (c=0.8; H$_2$O)

EXAMPLE 3

Example 1 was repeated except that 158 g of heavy liquor with a dianhydro sorbitol content of 84% by weight, based on dry matter, was placed in the crystallizer and 1 g of seed crystals was added. Stirring was maintained for 4 hours at 33° C.

The yield of 1,4:3,6-dianhydro-D-sorbitol was 39 g (30.9% of theory). It had the following properties:
Purity (HPLC): Greater than 99%
Melting Point: 61° C.
Rotation: $[a]_D^{20} = +44.8°$ C. (c=0.8; H$_2$O)
Water Content: Less than 0.5%

EXAMPLE 4

Example 1 was repeated except that 14,429 g of heavy liquor with a dianhydro sorbitol content of 75% by weight, based on dry matter, was placed in the crystallizer and 100 g of seed crystals were added. The mixture is cooled from 45° C. to 30° C. during 24 hours.

The yield of 1,4:3,6-dianhydro-D-sorbitol was 4200 g (40.4% of theory). It had the following properties:
Purity (HPLC): Greater than 99%
Melting Point: 60.7° C.
Rotation: $[a]_D^{20} = +44.4°$ C. (c=0.8; H$_2$O)
Water Content: Less than 0.5%

EXAMPLE 5

Example 1 was repeated except that 200 g of anhydropolyol mixture, containing 10% by weight of water and with a dianhydro mannitol content of 96% by weight, based on dry matter, was placed in the crystallizer at a temperature of 60° C., and 0.5 g of 1,4:3,6-dianhydro-D-mannitol seed crystals was added. The mixture was cooled from 60° C. to 40° C. during 12 hours.

The yield of 1,4:3,6-dianhydro-D-mannitol was 72 g (41.6% of theory). It had the following properties:
Purity (HPLC): Greater than 99%
Melting Point: 86.5° C.
Rotation: $[a]_D^{20} = +92.2°$ C. (c=1; H$_2$O)
Water Content: Less than 0.5%

EXAMPLE 6

Example 5 was repeated except that 100 g of anhydropolyol mixture, containing 5% by weight of water and with a dianhydro mannitol content of 75% by weight, based on dry matter, was placed in the crystallizer and 3 g of seed crystals were added. The mixture was cooled from 42° C. to 30° C. during 12 hours.

The yield of 1,4:3,6-dianhydro-D-mannitol was 43 g (60% of theory). It had the following properties:
Purity (HPLC): Greater than 99%
Melting Point: 86° C.
Rotation: $[a]_D^{20} = +92°$ C. (c=1; H$_2$O)
Water Content: Less than 0.5%

EXAMPLE 7

Example 1 was repeated except that 100 g of heavy liquor containing 7.5% by weight of water and with a 1,4-monoanhydro-D-sorbitol content of 66% by weight, based on dry matter, was placed in the crystallizer at a temperature of 55° C. and 1 g of 1,4-anhydro-D-sorbitol seed crystals was added. The mixture was cooled from 55° C. to 30° C. during 18 hours.

The yield of 1,4-monoanhydro-D-sorbitol was 36 g (58.9% of theory). It had the following properties:
Purity (HPLC): Greater than 99%
Melting Point: 115° C.
Rotation: $[a]_D^{20} = -22°$ C. (c=1; H$_2$O)
Water Content: Less than 0.5%

What is claimed is:

1. A process for recovering a pure crystalline anhydro sugar alcohol selected from the group consisting of 1,4-monoanhydro-D-sorbitol, 1,4:3,6-dianhydro-D-sorbitol, and 1,4:3,6-dianhydro-D-mannitol from an aqueous mixture, obtained by the acid-catalyzed dehydration of the corresponding sugar alcohols, of which at least 40% by weight on a dry solids basis is the desired anhydro sugar alcohol which consists of the sequential steps of
    (a) concentrating the mixture to a heavy liquor with a dry solids content of at least 70% by weight;
    (b) adjusting the temperature of the concentrated mixture to not more than 70° C.;
    (c) inoculating the concentrated mixture with at least 0.1% by weight of the mixture of seed crystals of the desired anhydro sugar alcohol;
    (d) stirring the inoculated mixture at such a rate as to promote crystallization of the anhydro sugar alcohol;
    (e) maintaining the supersaturation of the mixture with respect to the anhydro sugar alcohol being crystallized in the range where the existing crystals continue to grow without the spontaneous formation of new seed crystals; and
    (f) separating the crystalline anhydro sugar alcohol from the mixture.

2. The process of claim 1 wherein the supersaturation of the mixture is maintained in the desired range by lowering the temperature of the mixture at a rate not to exceed 0.1° C. per minute.

3. The process of claim 2 wherein the temperature of the mixture is lowered at a rate of between about 0.01° C. per minute and 0.05° C. per minute.

4. The process of claim 1 wherein the supersaturation of the mixture is maintained in the desired range by evaporating water from the mixture.

5. The process of claim 1 wherein the supersaturation of the mixture is maintained by adding heavy liquor to the mixture.

6. The process of claim 1 wherein the heavy liquor has a water content of from 1% to 20% by weight.

7. The process of claim 6 wherein the heavy liquor has a water content of from 2% to 15% by weight.

8. The process of claim 7 wherein the heavy liquor has a water content of from 3% to 8% by weight.

9. The process of claim 1 wherein from about 50% to about 99% by weight of the reaction mixture on a dry solids basis is the desired anhydro sugar alcohol.

10. The process of claim 9 wherein from about 60% to about 95% by weight of the reaction mixture on a dry solids basis is the desired anhydro sugar alcohol.

11. The process of claim 10 wherein from about 75% to about 90% by weight of the reaction mixture on a dry solids basis is the desired anhydro sugar alcohol.

12. The process of claim 1 wherein the amount of seed crystals used to inoculate the concentrated mixture is from about 1% to about 5% by weight of the mixture.

13. The process of claim 1 wherein the crystallization is carried out at temperatures between 20° C. and 65° C.

14. The process of claim 1 wherein the crystallization is carried out at temperatures between 25° C. and 60° C.

15. The process of claim 1 wherein the crystallization is carried out at temperatures between 30° C. and 55° C.

16. The process of claim 3 characterized in that the water content of the heavy liquor is from 3% to 8% by weight, from about 75% to about 90% by weight of the reaction mixture on a dry solids basis is the desired sugar alcohol, the amount of seed crystals used to inoculate the concentrated mixture is from about 1% to about 5% by weight of the mixture, and the temperature of the concentrated mixture is adjusted to between 30° C. and 55° C.

17. The process of claim 1 characterized in that the separated crystalline anhydro sugar alcohol is washed with water or an aqueous solution of the anhydro sugar alcohol.

18. The process of claim 1 characterized in that the mother liquor from which the crystalline anhydro sugar alcohol is separated is further concentrated and treated as in steps (b) through (e) of claim 1 to give an additional crop of the same or a different crystalline anhydro sugar alcohol.

19. The process of claim 18 further characterized in that the mother liquor is first subjected to an acid-catalyzed dehydration before it is further concentrated.

* * * * *